(12) United States Patent  
Bornefalk et al.

(10) Patent No.: US 11,123,026 B2
(45) Date of Patent: Sep. 21, 2021

(54) ENHANCED SPECTRAL X-RAY IMAGING

(71) Applicant: Prismatic Sensors AB, Stockholm (SE)

(72) Inventors: Hans Bornefalk, Vallentuna (SE); Fredrik Grönberg, Stockholm (SE); Mats Danielsson, Täby (SE)

(73) Assignee: PRISMATIC SENSORS AB, Stockholm (SE)

( * ) Notice: Subject to any disclaimer, the term of this patent is extended or adjusted under 35 U.S.C. 154(b) by 18 days.

(21) Appl. No.: 16/705,785

(22) Filed: Dec. 6, 2019

(65) Prior Publication Data

US 2020/0261041 A1    Aug. 20, 2020

Related U.S. Application Data

(60) Provisional application No. 62/807,457, filed on Feb. 19, 2019.

(51) Int. Cl.
*A61B 6/00* (2006.01)
*A61B 6/03* (2006.01)

(52) U.S. Cl.
CPC ............. *A61B 6/40* (2013.01); *A61B 6/032* (2013.01)

(58) Field of Classification Search
CPC .................... A61B 6/40; A61B 6/032
See application file for complete search history.

(56) References Cited

U.S. PATENT DOCUMENTS

| | | | |
|---|---|---|---|
| 8,552,370 B2 * | 10/2013 | Schultz | G01V 5/0075 250/306 |
| 9,757,085 B2 | 9/2017 | Wang et al. | |
| 9,836,859 B2 | 12/2017 | Zou et al. | |
| 2004/0264626 A1 * | 12/2004 | Besson | A61B 6/563 378/4 |
| 2010/0303196 A1 * | 12/2010 | Zou | A61B 6/542 378/5 |

(Continued)

OTHER PUBLICATIONS

International Search Report issued in International Application No. PCT/SE2019/051238 dated Feb. 7, 2020.

(Continued)

*Primary Examiner* — Hugh Maupin
(74) *Attorney, Agent, or Firm* — Nixon & Vanderhye

(57) ABSTRACT

An x-ray imaging apparatus includes an x-ray source and detector with multiple detector elements. The source and detector are on a support that rotates around a subject, enabling projections at different view angles. The apparatus operates the x-ray source in switched kVp mode for alternately applying different voltages, including lower and higher voltages, during rotation to enable lower-energy and higher-energy exposures over the projections, providing for lower-energy projections and higher-energy projections. The x-ray detector is a photon-counting multi-bin detector allocating photon counts to multiple energy bins, and the apparatus selects counts from at least a subset of the bins to provide corresponding photon count information for both lower- and higher-energy projections. The apparatus performs material basis decomposition for some of the lower-energy projections and higher-energy projections and/or for some combinations of at least one lower-energy projection and at least one higher-energy projection, based on the corresponding photon count information.

17 Claims, 11 Drawing Sheets

(56) References Cited

U.S. PATENT DOCUMENTS

2012/0087463 A1    4/2012  Greenberg et al.
2018/0235562 A1*  8/2018  Petschke ................ A61B 6/032

OTHER PUBLICATIONS

Alvarez, R., "Estimator for photon counting energy selective x-ray imaging with multibin pulse height analysis," Med. Phys. 38(5), May 2011, pp. 2324-2334.

Alvarez, R. and Macovski, A., "Energy-selective Reconstruction in X-ray Computerized Tomography," Phys. Med. Biol., 1076, vol. 21, No. 5, 733-744.

Ehn, S. et al., "Basis material decomposition in spectral CT using a semi-empirical, polychromatic adaptation of the Beer-Lambert model," Phys. Med. Biol. 62 (2017) N1.

Feby, S. et al., "Performance of today's dual energy CT and future multi energy CT in virtual non-contrast imaging and in iodine quantification: A simulation study," Med. Phys. 42 (7), Jul. 2015, pp. 4349-4366.

Tao, A. et al., "Dual-sourche photon counting detector CT with a tin filter: a phantom study on iodine quantification performance," Phys. Med. Biol. 64 (2019) 115019.

\* cited by examiner

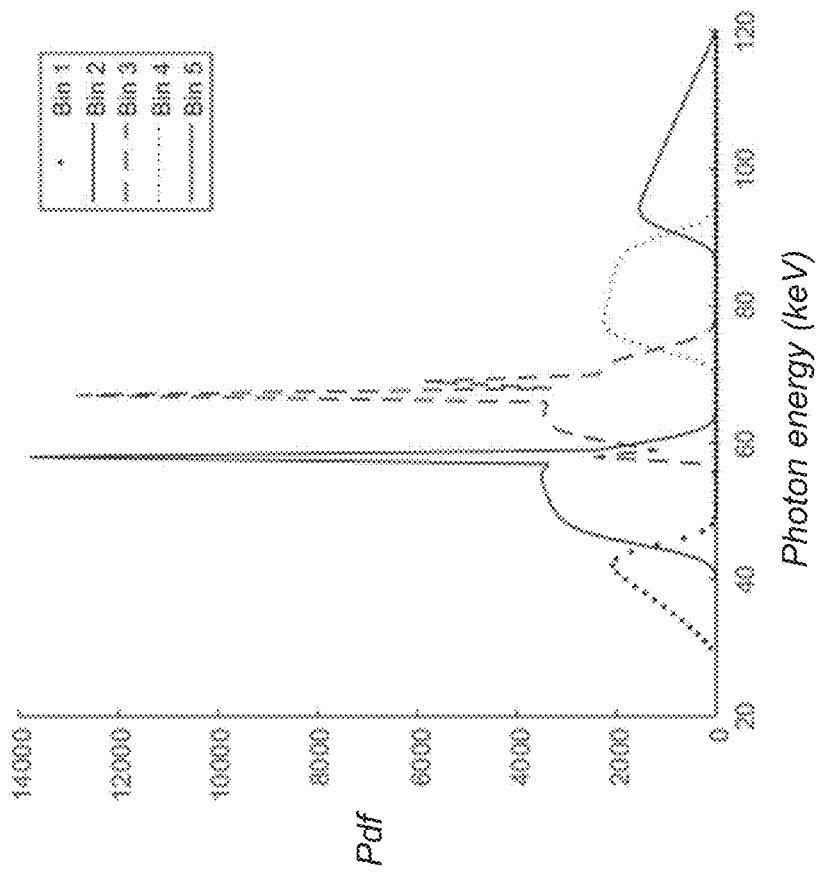
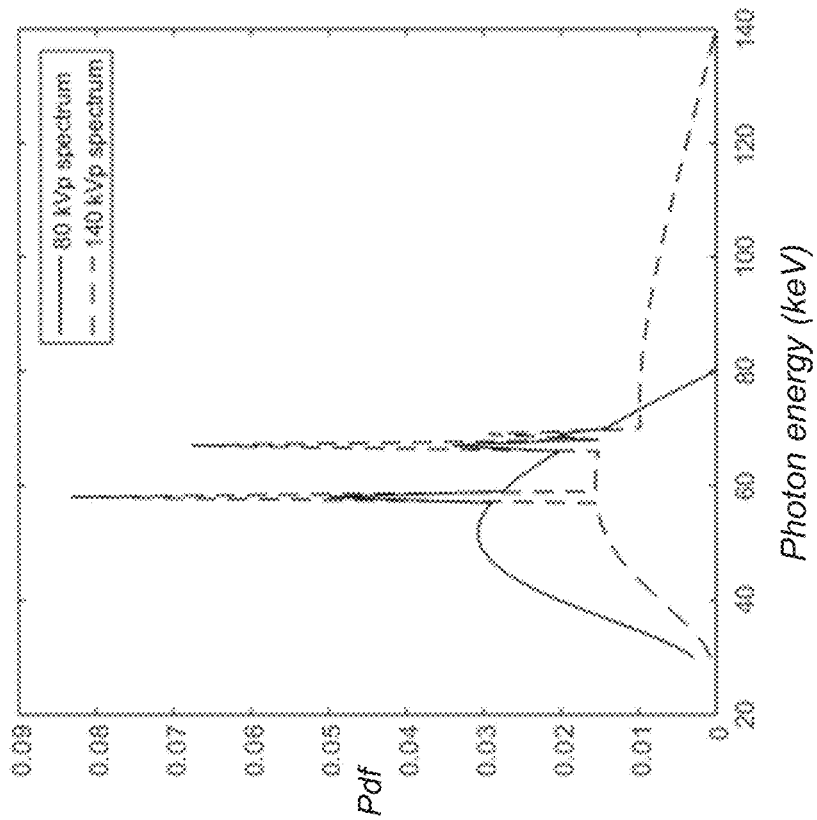
Fig. 2B
Fig. 2A

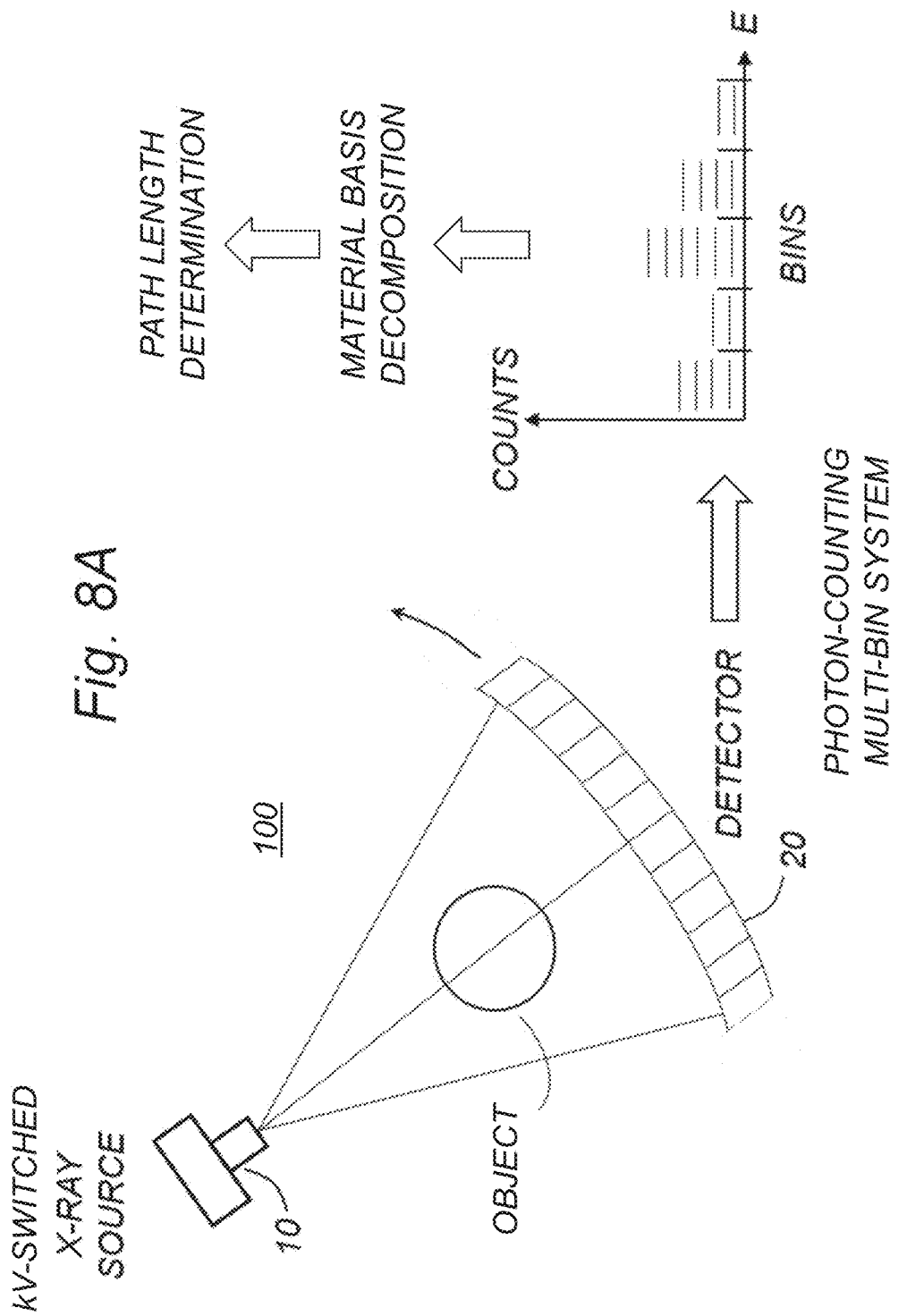

ENHANCED SPECTRAL X-RAY IMAGING

The project leading to this application has received funding from the European Union's Horizon 2020 research and innovation programme under grant agreement No 830294.

TECHNICAL FIELD

The proposed technology generally relates to x-ray imaging, and more particularly to an apparatus for x-ray imaging and a corresponding x-ray imaging system.

BACKGROUND

Radiographic imaging such as x-ray imaging has been used for years in medical applications and for non-destructive testing.

Normally, an x-ray imaging system includes an x-ray source and an x-ray detector consisting of multiple detector elements. The x-ray source emits x-rays, which pass through a subject or object to be imaged and are then registered by the detector. FIG. 1 is a schematic diagram illustrating an example of an incident x-ray spectrum vs. the actual deposited energies in the x-ray detector. Since some materials absorb a larger fraction of the x-rays than others, an image can be formed of the interior of the subject or object.

An x-ray Computed Tomography (CT) system includes an x-ray source and an x-ray detector arranged in such a way that projection images of the subject or object can be acquired in different view angles, normally covering at least 180 degrees. This is most commonly achieved by mounting the source and detector on a support or gantry that is able to rotate around the subject or object. An image containing projections registered in the different detector elements for the different view angles is called a sinogram. Normally, a collection of projections registered in the different detector elements for different view angles are referred to as a sinogram even if the detector is two-dimensional, making the sinogram a three-dimensional image.

An interesting development of x-ray imaging is energy-resolved x-ray imaging, also known as spectral x-ray imaging, where the x-ray transmission is measured for several different energy levels.

By way of example, this can be achieved by letting the x-ray source switch rapidly between two different emission spectra, or by using two or more x-ray sources emitting different x-ray spectra, in so-called dual-energy x-ray imaging. Typical implementations include:
  i) dual exposure (also known as spin-spin or rotate-rotate technique in which a low acceleration voltage is used during one full rotation followed by second full rotation at a higher acceleration voltage),
  ii) dual source (feeding two rotating x-ray tubes with different high voltages, typically around 80 kV and 140 kV),
  iii) rapid kV-switching (pulsing the x-ray tube with alternating high voltages, typically around 80 kV and 140 kV) and
  iv) dual layer techniques (sandwich detectors where the lower part of the detector sees effectively higher x-ray energies than the part closer to the source).

In a different approach to spectral x-ray imaging, an energy-discriminating detector is used which measures the incoming radiation in two or more energy levels. An example of such a detector is a photon-counting multi-bin detector, where each registered photon generates a current pulse which is compared to a set of thresholds, thereby counting the number of photons incident in each of a number of energy bins.

By way of example, photon counting detectors are outlined in references [1, 2].

In reference [3], at least one energy threshold is adjusted in accordance with the kV-waveform used by the radiation source, so that detected photon counts in the respective spectral bins are substantially equalized.

The methods and reasons for wanting to perform spectral x-ray imaging are well-described in the literature. The clinical reasons in the case of x-ray computed tomography imaging encompass artefact removal and contrast enhancement. The methods are based on the ability to perform material basis decomposition whereby, in short, the full energy dependence of the linear attenuation coefficients of human tissue can be determined by using the fact that linear attenuation coefficients of human tissue are well described as a linear combination of two energy basis functions.

Faby et al [4] present a simulation study where the potential benefit of using photon counting detectors based on CdTe in combination with dual source spectra (see point ii above) is explored (two x-ray tubes). Table II of Faby et al shows that image quality benefits can be obtained above both those of dual source with energy integrating detectors and also above those of single source photon counting multi-bin CT if a realistic response model of CdTe is used.

Measurements from an experimental multi-source (dual source) photon-counting-detector CT based on CdTe have been presented in November 2018 at RSNA [5]. The experimental setting is based on a photon-counting detector in combination with two x-ray spectra (dual source), although a spin-spin or rotate-rotate approach to dual energy was applied, i.e. one full rotation using a low acceleration voltage followed by second full rotation at a high acceleration voltage, due to system limitations.

Photon counting spectral CT utilizing photon counting multi-bin detectors improves upon the capabilities of dual energy CT. Having estimated the linear attenuation coefficient at more than two distinct energies allows for more advanced image reconstruction, for example k-edge imaging. There is also a general understanding that even for simpler reconstruction tasks, for instance 2-basis-material decomposition (i.e. not utilizing the k-edge of any contrast agent such as iodine, gadolinium or gold nanoparticles), image quality is enhanced due to a reduction of spectral overlap.

Spectral overlap refers to the overlap of the maximum á-posteriori (MAP) distributions of photon energies used to generate the two signals in dual energy imaging (one low-energy distribution and one high-energy distribution). Typically, heavy filtering with Sn or some other metal is applied to the high energy spectrum in dual source or switched kVp to reduce the amount of overlap. This increases the difference between the average energies of the high and low energy spectra (increased spectral separation) and thereby allows for better estimation of the linear attenuation coefficient. Photon counting detectors, at least if they are ideal photoelectric absorbers, have limited overlap between the bins and large spectral separation.

If an ideal photon counting detector places an event in an energy bin defined by the upper and lower limits $T_i, T_{i+1}$ in keV, one knows that the original x-ray energy obeyed $T_i < E < T_{i+1}$ rather than the relatively more uncertain knowledge that it emanated from either a low- or a high-energy spectrum as would be the case for dual energy techniques. This is illustrated in FIG. 2A and FIG. 2B, where the maximum-a posteriori (MAP) estimates of the incident probability density function of actual photon energy is illustrated for two example systems.

FIG. 2A is a schematic diagram illustrating an example of maximum-a posteriori (MAP) estimates of the incident probability density function of photon energy for a switched kV system fed by 80 and 140 kV. If a photon is detected when the tube was operated at 80 kV, the solid line illustrates the best educated guess (in terms of a distribution) that can be made regarding its original energy. The dashed line is the maximum á posteriori estimate of the incident energy when the tube was operated at 140 kV. These are just the incident-ray spectra since no additional information is available.

FIG. 2B is a schematic diagram illustrating an example of similar maximum a posteriori-estimates for an ideal photon counting multi-bin system with the photo-electric effect as sole interaction mechanism. Here the line centered around 80 keV is the best estimate of the actual photon energy if a photon from a 120 kVp spectrum is detected in the third bin defined by its edges 74 and 91 keV. The overlap stems from a limited but realistic energy resolution and clearly shows the concept of reducing spectral overlap and thereby obtaining more accurate estimate of incident energy, something that is beneficial in image reconstruction.

In other words, FIG. 2A shows depicts the MAP probability distribution of the incident x-ray energy for a dual energy system (without heavy filtering of the 140-kVp spectrum), and FIG. 2B the same for a photon-counting multi-bin detector system. The illustrative photon-counting system has a photoelectric detector, i.e. all energy of the incident photon is converted.

In FIG. 2A, the 80 kVp-spectrum line is the best estimate of the x-ray energy given the information that it was detected during the 80-kV exposure, and equivalently for the 140-kV exposure. They are highly non-informative and just depicts the two incident x-ray spectra, and it can be seen that the spectra overlap from 30 to 80 keV. In FIG. 2B, there is a clearer separation of energies and the overlap of MAP estimates of energies, depending on in which bin 1-5 the event was detected, is smaller.

Real photon counting detectors typically have a response function that is not ideal. If cadmium-zink-telluride (CZT) or cadmium telluride (CdTe) is used, there will be a large low-energy tail of the response. If silicon is used, Compton interactions will result in less than complete conversion of the incident x-ray energy. In both these cases the detected energy will be less than the actual photon energy. This is illustrated in FIG. 3, where the responses to a 70 keV-x ray are shown for a silicon detector (dotted line) and a CZT detector (dashed line), respectively.

When the response of such more realistic response functions is inverted, to determine the actual photon energy from the detected energy; i.e. to determine the MAP estimate, the result is again spectral overlap which tends to decrease overall imaging performance.

There is thus a general demand for improved spectral x-ray imaging.

SUMMARY

It is a general object to provide technical solutions for enhanced spectral imaging.

It is a specific object to provide an apparatus for x-ray imaging and a corresponding x-ray imaging system.

These and other objects may be achieved by one or more embodiments of the proposed technology.

According to a first aspect, there is provided an apparatus for x-ray imaging comprising an x-ray source and an x-ray detector having a number of detector elements, wherein the x-ray source and the x-ray detector are arranged on a support that is able to rotate around a subject or object to be imaged to enable a set of projections at different view angles. The apparatus is configured to operate the x-ray source in so-called switched kVp mode for alternately applying at least two different voltages, including a lower voltage and a higher voltage, during rotation to enable lower-energy and higher-energy exposures over the set of projections, thereby providing for lower-energy projections and higher-energy projections. The x-ray detector is a photon-counting multi-bin detector configured to allocate photon counts to multiple energy bins, and the apparatus is configured to select counts from at least a subset of the energy bins to provide corresponding photon count information for both lower-energy projections and higher-energy projections. The apparatus is further configured to perform material basis decomposition for each of a number of the lower-energy projections and higher-energy projections and/or for each of a number of combinations of at least one lower-energy projection and at least one higher-energy projection, based on the corresponding photon count information.

This technological solution involving a very specific combination of key features enables enhanced spectral x-ray imaging.

According to a second aspect, there is provided an x-ray imaging system comprising an apparatus for x-ray imaging.

BRIEF DESCRIPTION OF DRAWINGS

The embodiments, together with further objects and advantages thereof, may best be understood by making reference to the following description taken together with the accompanying drawings, in which:

FIG. 2A is a schematic diagram illustrating an example of maximum-a posteriori (MAP) estimates of the incident probability density function of photon energy for a switched kV system fed by 80 and 140 kV.

FIG. 2B is a schematic diagram illustrating an example of similar maximum a posteriori-estimates for an ideal photon counting multi-bin system with the photo-electric effect as sole interaction mechanism.

FIG. 8A is a schematic diagram illustrating an example of relevant parts of an x-ray imaging system according to an embodiment.

DETAILED DESCRIPTION

Figure 1:
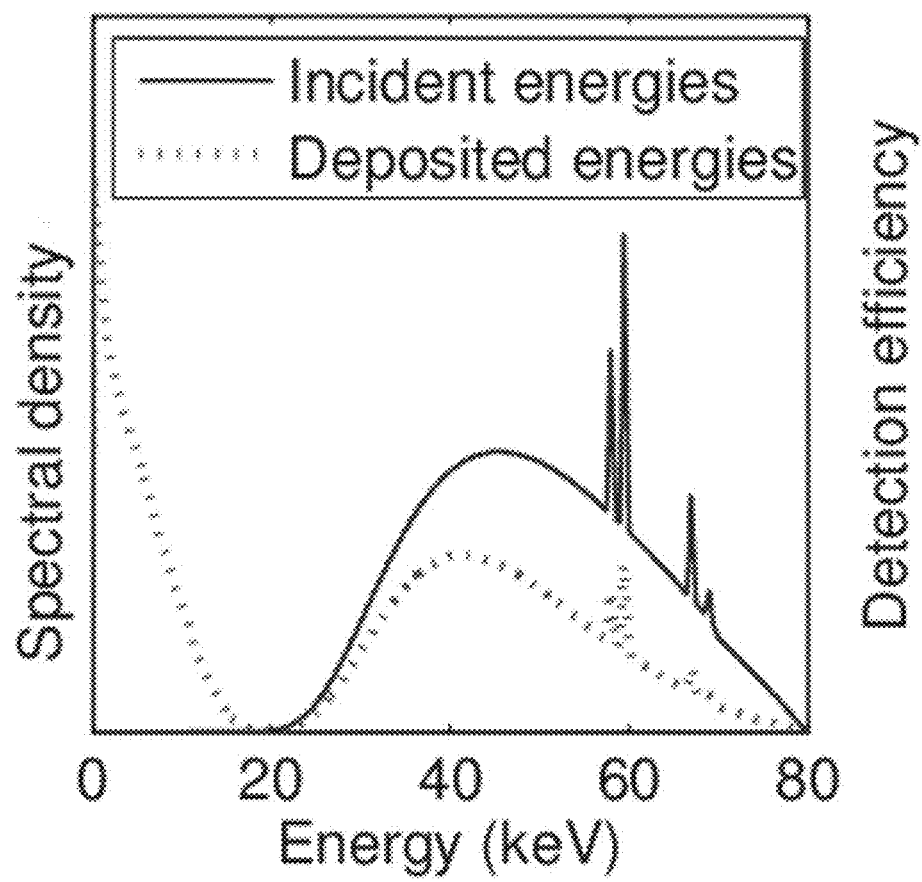
FIG. 1 is a schematic diagram illustrating an example of an incident x-ray spectrum vs. the actual deposited energies in the x-ray detector.
Figure 3:
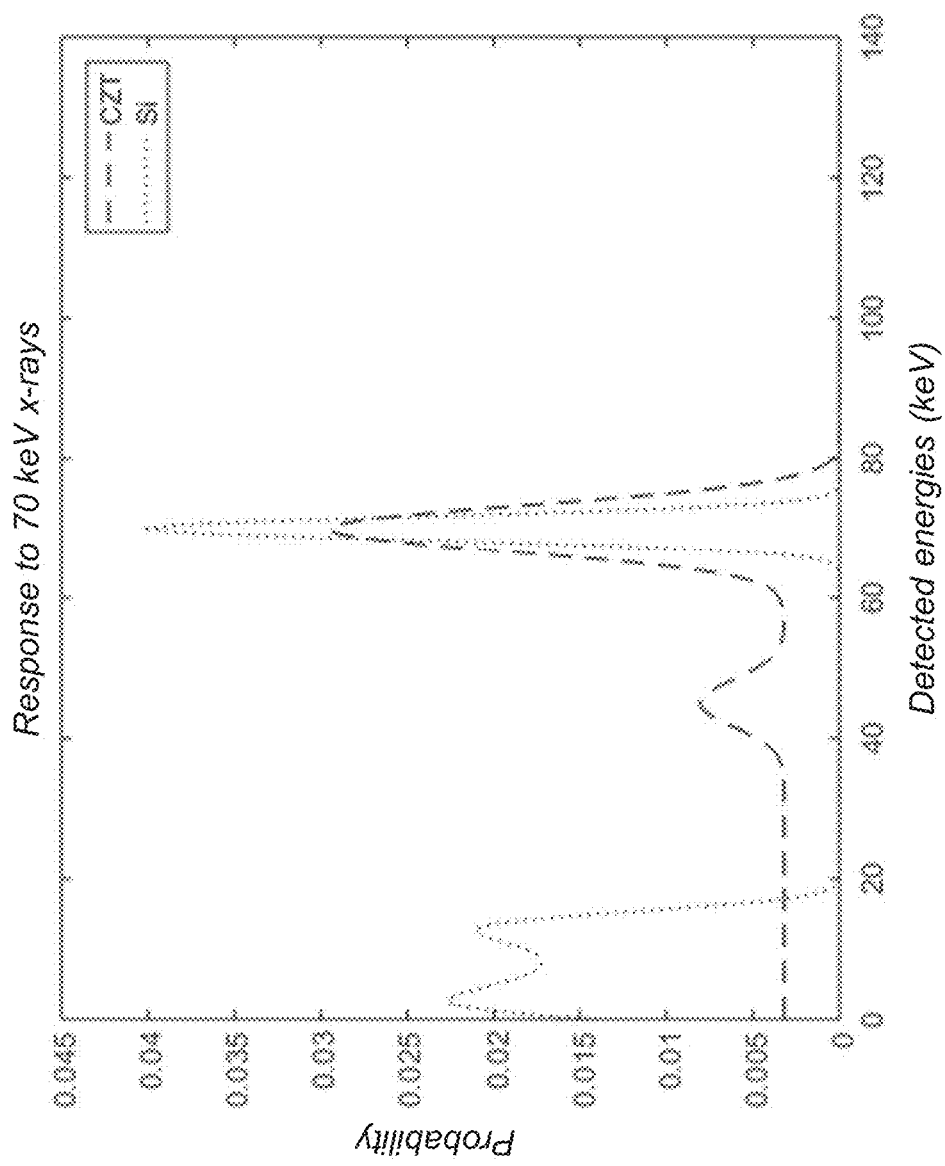
FIG. 3 is a schematic diagram illustrating an example of detector responses to a 70 keV-x ray for a silicon detector (dotted line) and a CZT detector (dashed line), respectively.

In the following we refer to energy integrating x-ray detectors as detectors where the incremental output signal from one additional interacting photon of energy E (keV) is proportional to E. Detectors where a counter is incremented if E is above a certain threshold are denoted photon counting detectors. Finally, photon counting multi-bin detectors refer to detectors with several thresholds and counters and where the counters are incremented dependent on the relationship between the deposited energy E and the threshold settings.

When referring to dual energy techniques for x-ray imaging in general and Computed Tomography (CT) in particular, solutions are considered whereby two different efficient x-ray spectra are used in the image generation. As a mentioned, typical implementations include dual exposure (also known as spin-spin or rotate-rotate technique), dual source (feeding two rotating x-ray tubes with different high voltages, typically around 80 kV and 140 kV), rapid kV-switching (e.g. pulsing the x-ray tube with alternating high voltages, typically around 80 kV and 140 kV) and dual layer techniques (sandwich detectors where the lower part of the detector sees effectively higher x-ray energies than the part closer to the source).

In order to resolve some of the challenges for improving spectral x-ray imaging, the proposed technology provides an apparatus for x-ray imaging comprising an x-ray source and an x-ray detector having a number of detector elements, wherein the x-ray source and the x-ray detector are arranged on a support that is able to rotate around a subject or object to be imaged to enable a set of projections at different view angles. The apparatus is configured to operate the x-ray source in so-called switched kVp mode for alternately applying at least two different voltages, including a lower voltage and a higher voltage, during rotation to enable lower-energy and higher-energy exposures over the set of projections, thereby providing for lower-energy projections and higher-energy projections. The x-ray detector is a photon-counting multi-bin detector configured to allocate photon counts to multiple energy bins, and the apparatus is configured to select counts from at least a subset of the energy bins to provide corresponding photon count information for both lower-energy projections and higher-energy projections. The apparatus is further configured to perform material basis decomposition for each of a number of the lower-energy projections and higher-energy projections and/or for each of a number of combinations of at least one lower-energy projection and at least one higher-energy projection, based on the corresponding photon count information.

This technological solution, involving a very specific combination of key features, enables enhanced spectral x-ray imaging.

By way of example, the present invention proposes using the rapidly switched kV-technique combined with photon-counting multi-bin x-ray detectors, for example photon counting multi-bin detectors with silicon as direct conversion material. A part of the solution is to integrate the use of a specific dual- or multi-energy technique, namely switched kV, with a photon-counting multi-bin x-ray detector to provide for both lower-energy projections and higher-energy projections during a rotation (possibly during each rotation) and employ the multi-bin x-ray detector to provide photon count information for these projections. The idea is then to perform material basis decomposition for each of a number of the lower-energy projections and higher-energy projections and/or for each of a number of combinations of at least one lower-energy projection and at least one higher-energy projection, based on the corresponding photon count information.

The proposed technology is especially useful together with material basis decomposition to improve image reconstruction and/or image quality. The reason is that more information can be extracted from otherwise fairly non-informative low-energy Compton events depositing a mere 5-10 keV in the detector.

Figure 4:
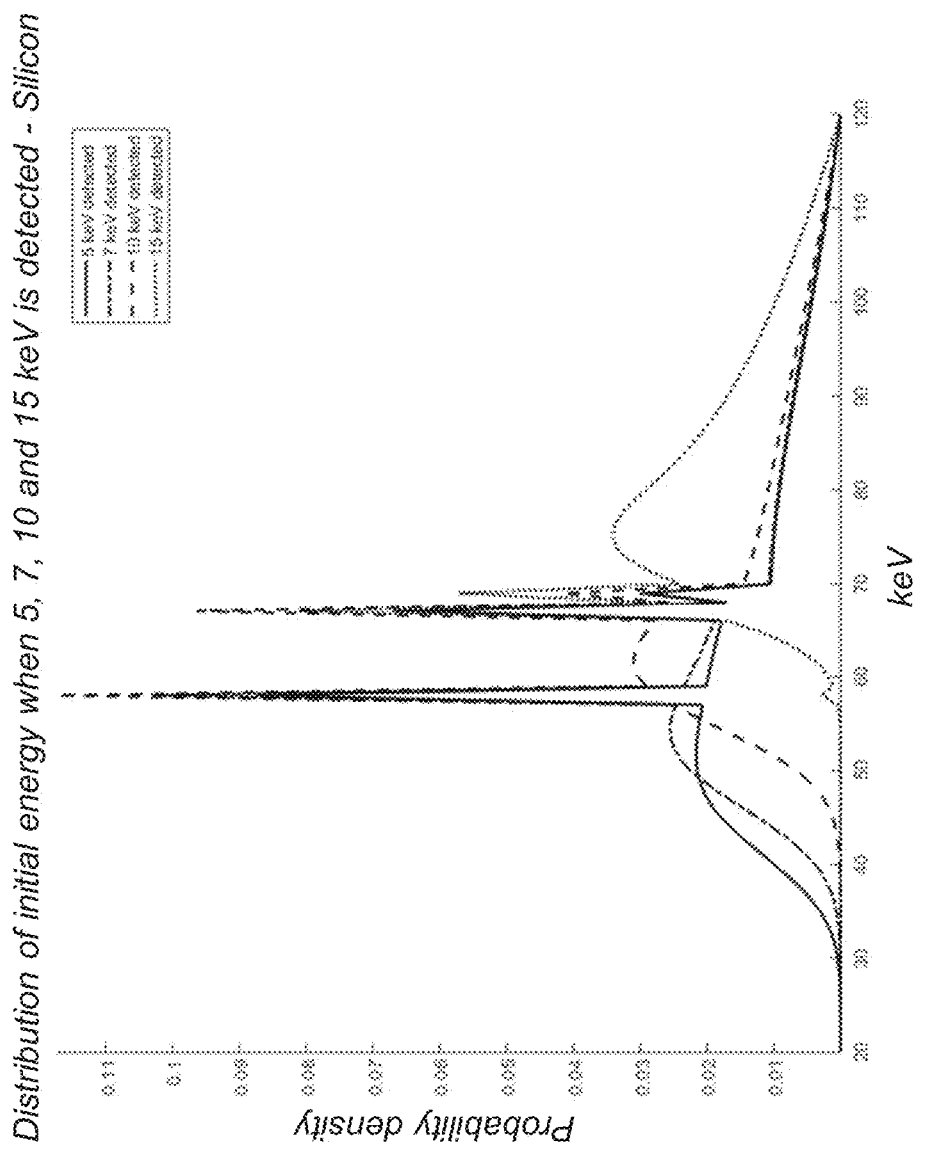
FIG. 4 is a schematic diagram illustrating an example of MAP estimates of the incident energy for events depositing 5, 7, 10 and 15 keV in a silicon detector.

FIG. 4 is a schematic diagram illustrating an example of MAP estimates of the incident energy for events depositing 5, 7, 10 and 15 keV in a silicon detector. For 5 and 7 keV events, the MAP estimate closely resembles the incident spectrum, i.e. knowledge of the fact that 5 or 7 keV was deposited does not add extra information. Keeping in mind that a response function can be inverted to determine the actual photon energy from the detected energy (the MAP estimate).

If switched kV is used, i.e. rapidly alternating the acceleration voltage during rotation such that typically one half or two thirds of the projections see a softer x-ray spectrum (for example 80 or 90 kVp instead of 140 or 150 kVp), the MAP estimates of the energy distribution will differ for low-voltage projections and high voltage projections. Indeed, the MAP estimates of the incident energy for an event depositing 5 keV, when 80 and 140 kV are applied, will look like FIG. 2A: two distinct distributions owing to the fact that different prior information regarding the incident x-ray spectrum exists. Therefore, it is clear that additional information has been introduced.

Both the measurement and the simulation study of reference [5] indicate that there is a benefit in spectral imaging to combine a general dual-energy approach with photon counting detectors. However, if two x-ray tubes (typically mounted 90 degrees apart on the rotating gantry) or a spin-spin approach to dual energy as suggested in [5], there will be a relatively large delay in time between the low-energy x-ray exposure and the high-energy x-ray exposure of the object. In the case of dual source, this time is a quarter of the time of a revolution and in the spin-spin approach it is the full revolution time. A typical revolution time in CT is 0.3-0.5 seconds. When imaging a beating heart or other moving structures this time delay typically results in substantial motion artifacts.

Rapidly switching kV resolves this, by alternating between high- and low-energy exposures during a revolution. Typically, a low-energy exposure is applied in one or two projections/views, followed by one high-energy exposure in the next projection/view which is again followed by one or two projections/views with low-energy exposures and so on until all desired projections/views are collected (a view is the exposure with the gantry in a certain rotation angle). For example, 2000 views typically make a full rotation of the gantry.

The proposed technology thus encompasses a method and corresponding apparatus combining the benefits of kV-switching with photon counting multi-bin x-ray detectors such as photon counting multi-bin silicon detectors, especially for use with extended material basis decomposition to improve image reconstruction and/or image quality.

For each of a number of lower-energy and higher-energy projections during rotation of the gantry of a CT system or similar x-ray imaging system with a kV-switched x-ray source, photon-count information including photon counts allocated to different energy bins may be acquired to provide spectral information for basis material decomposition and/or image reconstruction.

In general, switched kVp, also called to as kV-switched operation, or rapid kV-switching, refers to alternately applying at least two different voltages, including a lower voltage and a higher voltage, to the x-ray source during rotation to enable lower-energy and higher-energy exposures over a set of projections. The term kVp refers to peak kilovoltage, which means the maximum high voltage applied across the x-ray tube, corresponding to the highest kinetic energy of electrons striking the target of the x-ray source when producing the x-rays, and being proportional to the maximum energy of the resulting x-ray emission spectrum.

Hence, the apparatus may be configured to provide rapid kV-switching for alternately applying at least two different voltages to the x-ray source during a rotation (possibly during each rotation).

By way of example, with reference to e.g. FIG. 8A, the photon-counting multi-bin detector may be configured to allocate, for each projection, i.e. for each detector element and each view angle, under a lower-energy or higher-energy exposure, photon counts to energy bins, and the apparatus may be configured to extract counts from at least a subset of the energy bins to provide corresponding photon count information for the projection.

For example, the apparatus may be configured to perform the material basis decomposition to generate pathlength estimates of basis materials for each of a number of the lower-energy projections and higher-energy projections and/or for each of a number of combinations of at least one lower-energy projection and at least one higher-energy projection, and to perform image reconstruction based on the path length estimates.

For example, the apparatus may be configured to perform material basis decomposition based on information about the applied x-ray spectrum.

In a particular example, the apparatus is configured generate a dual energy path length estimate based on adjacent projections, including photon count information of at least one lower-energy projection and at least one higher-energy projection.

As an example, the apparatus may be configured to use the dual energy path length estimate as prior information to optimize the trade-off between spatial resolution and basis image noise.

For example, the dual energy path length estimate may be used in a penalty function for compensating for reduced spatial resolution due to adjacent projections having different view angles.

Optionally, the apparatus may be configured to generate pathlength estimates for basis materials and associated covariance matrices representing covariance of the estimated pathlengths, and to combine pathlength estimates for lower-energy and higher-energy projections based on the corresponding covariance matrices.

By way of example, the apparatus may be configured to selectively perform a weighting procedure in dependence on a selected imaging task.

Optionally, thresholds of the photon counting multi-bin detector are allocated such that one or more bins are allocated to count the Compton part of the spectrum and the remainder is allocated to the photo-electric part of the spectrum.

In this way, the apparatus may be configured, e.g. to use counts in the bins from the photo-electric part of the spectrum to perform material basis decomposition in the projection domain using a maximum likelihood-approach or based on a linearization thereof, and to use counts in the Compton part of the spectrum for a dual energy like material basis decomposition, as will be exemplified in more detail later on.

Thresholds of the photon counting multi-bin detector for higher- and lower-energy projections may be the same, or thresholds of the photon counting multi-bin detector for lower-energy projections may differ from thresholds for higher-energy projections.

For example, the photon-counting multi-bin detector may be based on a direct conversion material. Preferably, the photon-counting multi-bin detector is provided with silicon as the direct conversion material.

Complementary, there is provided an x-ray imaging system comprising an apparatus for x-ray imaging as described herein.

By way of example, the x-ray imaging system and/or the apparatus for x-ray imaging is may be a Computed Tomography (CT) system.

In the following, the proposed technology will be described with reference to non-limiting examples.

For example, the apparatus may be implemented by a third generation CT scanner with a single x-ray tube rotating around an object to be imaged. For example, the detector comprises silicon sensors operated in photon-counting multi-bin mode. The x-ray tube is further equipped with means for rapid kV-switching. During a scan projection, data is obtained either in regular mode, feeding the x-ray tube a constant voltage, or in a switched mode, where some projections see a relatively lower acceleration voltage and the rest a higher acceleration voltage. The detector allocates counts to energy bins where the thresholds for high- and low-energy projections may or may not be the same.

In a particular example, for each projection, the counts in the bins are used to perform material basis decomposition in the projection domain or in the image domain taking knowledge of the actual shape of the incident x-ray spectrum for that particular projection into account. This can be done in different ways. In an example embodiment, maximum likelihood estimation is performed. In another embodiment, calibration phantom measurements have been acquired using otherwise identical tube settings (at least one using a relatively lower acceleration voltage and at least one with a relatively higher voltage, preferably acquired in rapid switching mode so any afterglow or other focal spot effects will be identical to those under a clinical scan). The results from the calibration measurement can be used for determining separate forward models according to reference [7] for the at least one high and at least one low energy spectrum. Such an approach captures the different low energy and high energy spectral shape implicitly. Anyway, it is thus possible to employ or take (a priori) information on the used x-ray spectrum into account when performing basis decomposition and/or image reconstruction.

Figure 5B:
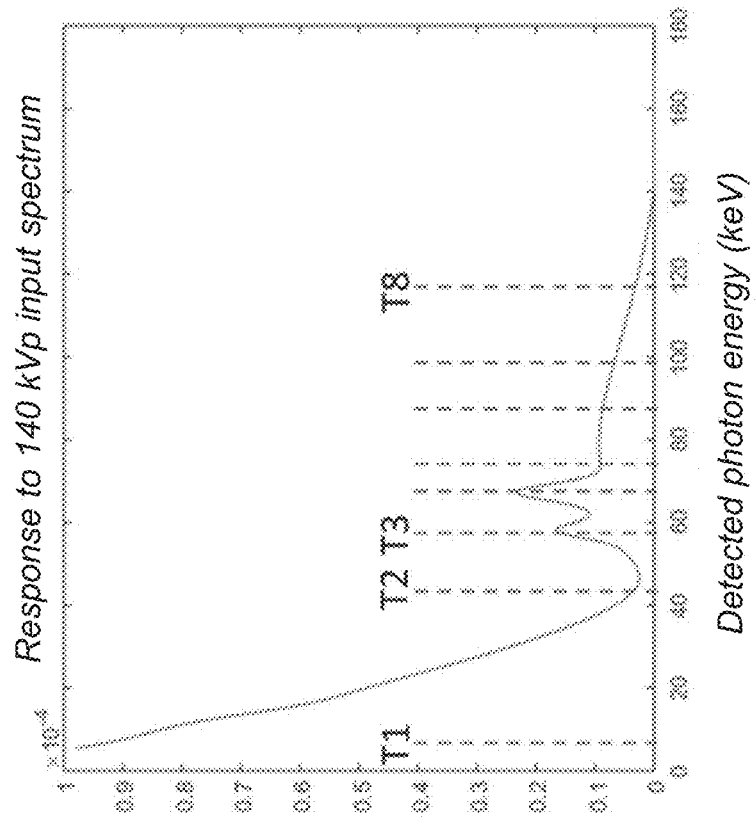
FIG. 5A and FIG. 5B are schematic diagrams illustrating the detector response to 80 kVp input spectrum and 140 kVp input spectrum, respectively.
Figure 5A:
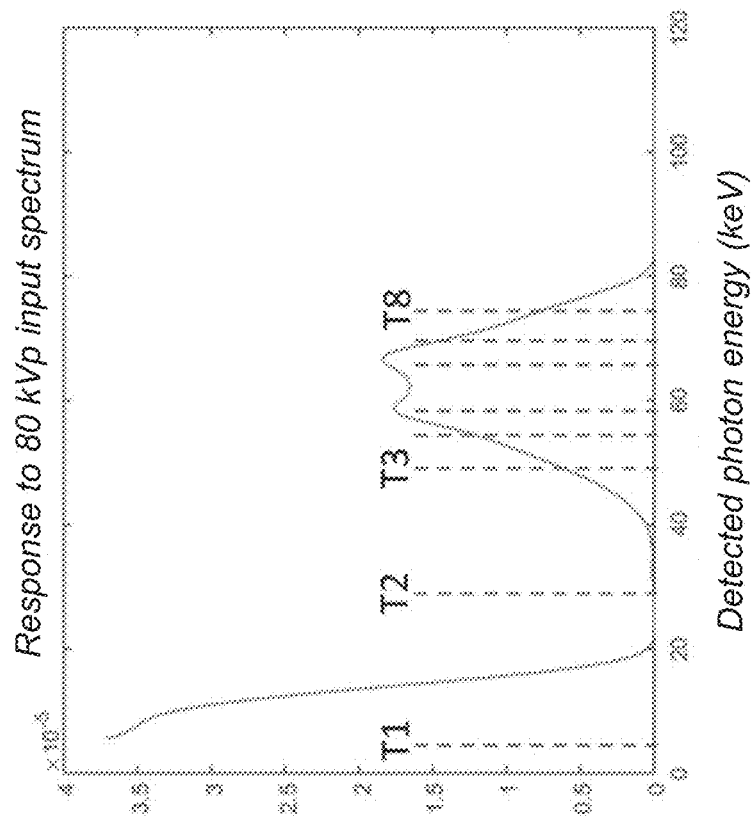

In yet another example embodiment, the thresholds of the photon counting multi-bin detector are allocated such that very few bins, possibly only one, are allocated to count the Compton part of the spectrum and the remainder is allocated to the photo-electric part of the spectrum. Dividing the spectrum of deposited energies into a Compton part and a photo electric part takes advantage of or is dependent on the direct conversion material being silicon and the concept is illustrated in FIG. 5A and FIG. 5B, where T1, T2, . . . , T8 denote thresholds defining the energy bins. In this particular example, there are thus 8 energy bins.

FIG. 5A and FIG. 5B are schematic diagrams illustrating the detector response to 80 kVp input spectrum and 140 kVp input spectrum, respectively. The solid line is a typical distribution of detected energies (pulse height spectrum) in the detector and dashed lines denoted T1, . . . , T8 are illustrative of energy thresholds used to group counts into bins.

In a particular example, the counts in the bins from the photo-electric part of the spectrum can be used to perform material basis decomposition in the projection domain using for example a maximum likelihood-approach or based on some linearization thereof as for instance the one outlined in [6]. The counts in the Compton part of the spectrum, possibly allocated in only one bin can be used for a dual energy like material basis decomposition in a similar fashion to current dual energy system using energy integrating detectors.

If three materials are to be decomposed, for example iodine, bone and soft tissue, it is possibly beneficial to have two bins allocated to the Compton parts of the spectra to get a total of four separate efficient energies allowing a decomposition into three or more basis materials.

If the material basis decomposition using data from the switched kVp mode is done separately in two paths for each kVp applied, one for the Compton events and one for the photo events, the result will be two separate estimates of the material path lengths. They will have the same expected value but different covariance matrices (covariance of the estimated pathlength of the two or more basis materials assumed). A weighting scheme such as inverse weighting, possibly depending on the imaging task, can be applied to arrive at the most efficient estimator (with the lowest variance) by weighted summation, possibly weighted by matrix multiplication, of the two independent estimates obtained from the low and the high energy spectra.

The use of a weighting scheme such as an inverse weighting scheme is applicable also to the cases where events are not explicitly designated as Compton events and processed using standard dual energy methods. If maximum likelihood or linearized versions thereof is applied, each projection in switched kV mode still generates pathlength estimates that have the same expected value but different covariance matrices and some (inverse) variance weighting is therefore desirable to perform. This is illustrated schematically in FIG. 6 and FIG. 7.

Figure 6:
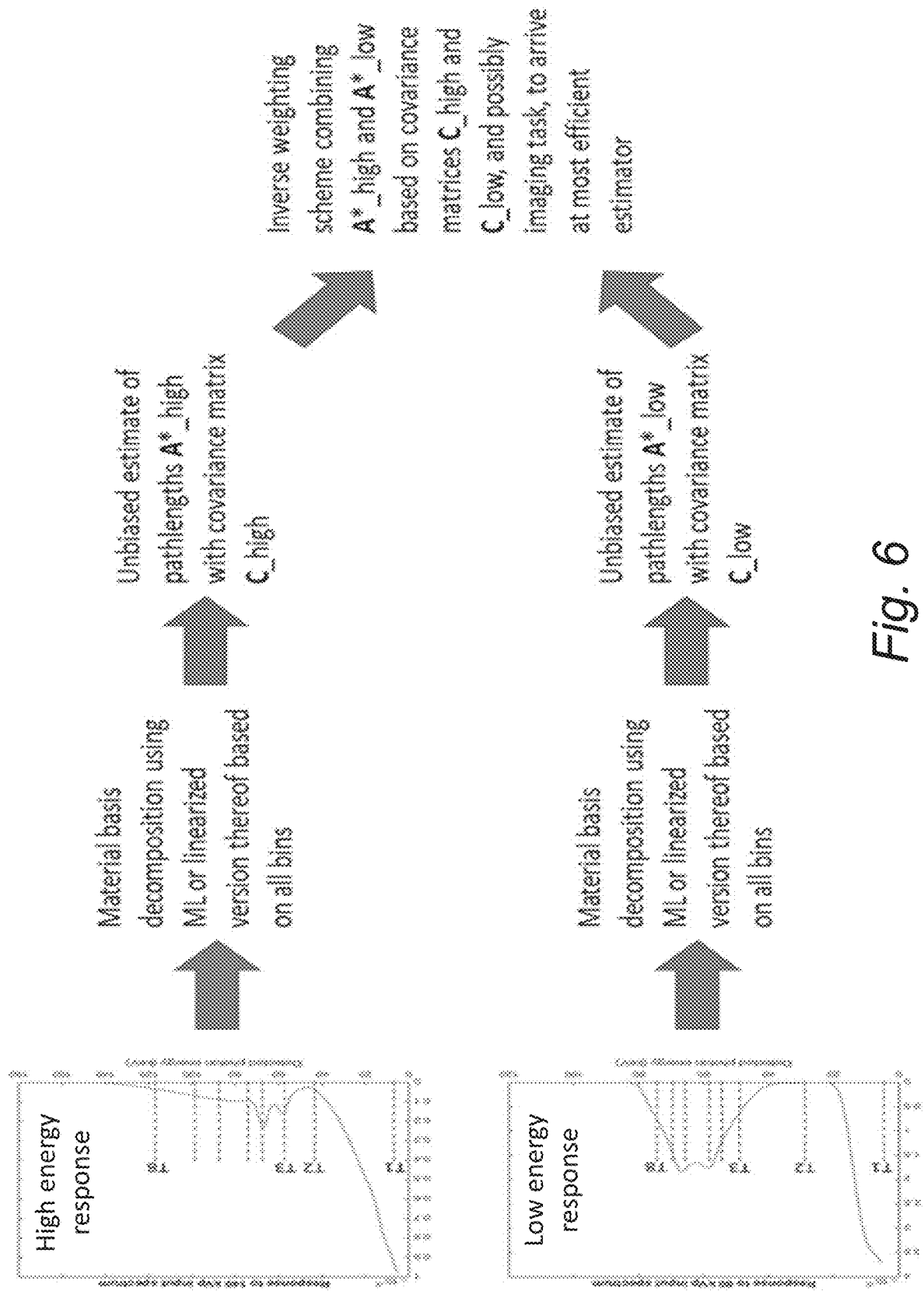
FIG. 6 is a schematic diagram illustrating an example of how the material basis estimation scheme operates on the data without making explicit use of dual energy processing of Compton events.

FIG. 6 is a schematic diagram illustrating an example of how the material basis estimation scheme operates on the data without making explicit use of dual energy processing of Compton events.

Figure 7:
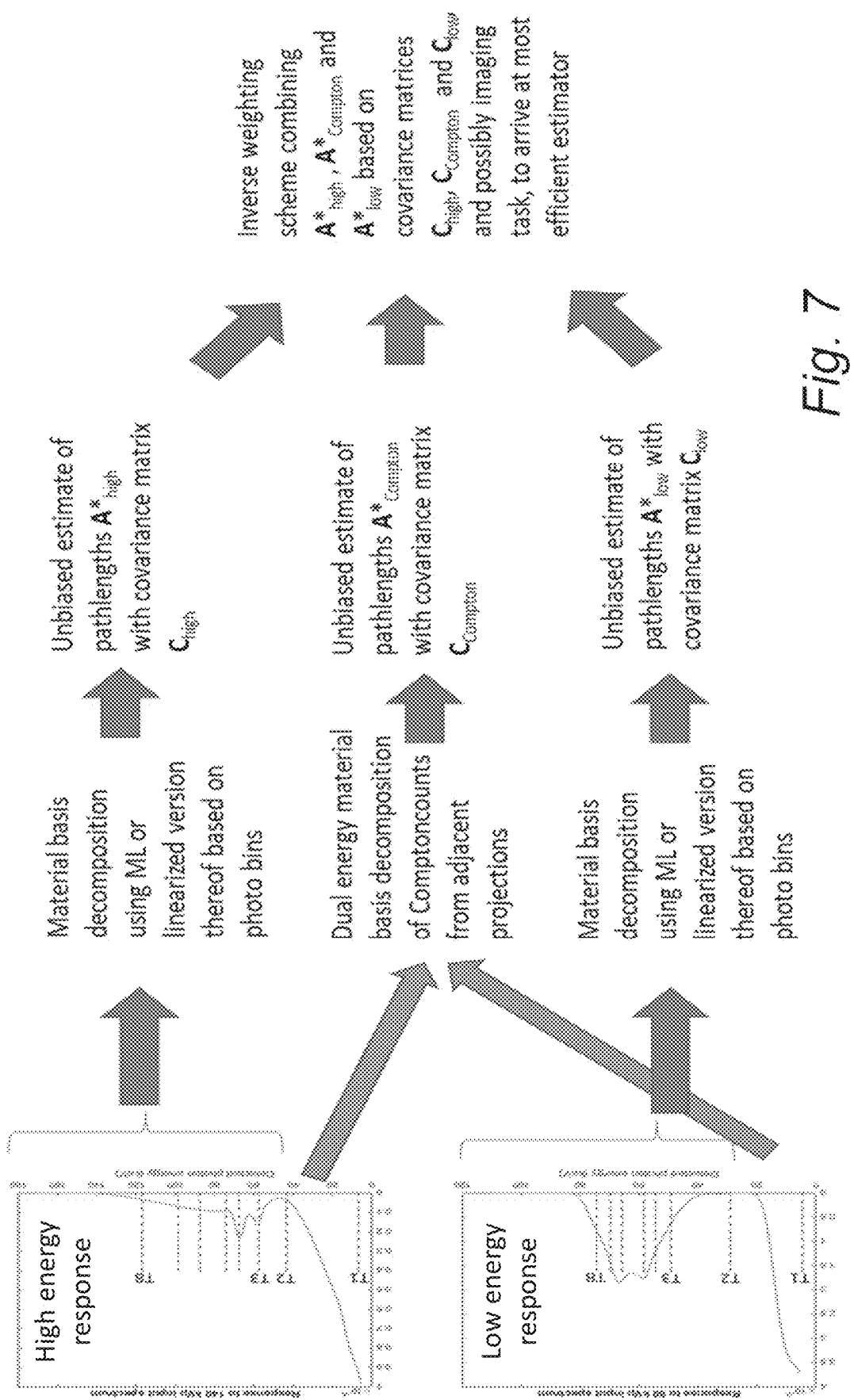
FIG. 7 is a schematic diagram illustrating an example of how the material basis estimation scheme operates on the data where explicit use is made of Compton events.

FIG. 7 is a schematic diagram illustrating an example of how the material basis estimation scheme operates on the data where explicit use is made of Compton events.

Note that the dual energy path length estimate will have to use two adjacent projections without perfect alignment. This slight misregistration, common for all switched kVp reconstruction methods where basis material decomposition is performed, might result in a loss of spatial resolution. This may or may not be taken into consideration in the (inverse) weighting scheme, depending on imaging task. The imaging task can also be used to determine which of the methods described in FIG. 6 and FIG. 7 is to be used. For example, if high spatial resolution is essential, a reconstruction path like the one outlined in FIG. 6 may be preferable and a path like in FIG. 7 may be preferable if low contrast resolution or image noise is preferable.

In yet another embodiment, material basis decomposition may be performed on several views binned. A typical such binning of views would be to take the counts from the N energy bins in a view that saw a low energy exposure and the counts from the N energy bins that saw a high energy exposure (in an adjacent view angle). In this example, that would yield 2N sets of counts, which would be slightly misaligned due to them being obtained at slightly different gantry angles. Material basis decomposition could be performed on the 2N counts. This information can be used as prior information (for instance by invoking a constraint in a maximum likelihood estimation) for a material basis decomposition of a high-fidelity data set as outlined in FIG. 6.

This information can be used as prior information for a material basis decomposition of high spatial resolution using the at least high- and low-energy data sets separately as outlined in FIG. 6. One possible way to use the prior information is to obtain a more desirable tradeoff between image contrast-to-noise ratio and spatial resolution (and possibly aliasing) by adding a penalty term in the native resolution material basis decomposition that depends on the pathlength deviation from the aggregate pathlength estimate.

The following example illustrates the idea:

If the N counts in a detector element y from a low-energy exposure are denoted $Y(\gamma, \theta_{low}) \in \mathbb{R}^N$ and the N counts in the same detector element but from an adjacent view with a high-energy exposure is denoted $Y(\gamma, \theta_{high})$, a combined view with 2N count are generated by concatenation of the two count vectors, $Y(\gamma, \bar{\theta}) \in \mathbb{R}^{2N}$ where $$\bar{\theta} = \frac{\theta_{low} + \theta_{high}}{2}.$$

If $F_{aggregate}$ is the forward model for the aggregated spectra, i.e. mapping from pathlengths to counts, $A \to Y \in \mathbb{R}^{2N}$, the maximum likelihood solution of pathlengths estimate is:

$A_{aggregate}*(\gamma\bar{\theta}) = \operatorname{argmin}_A \mathcal{L}(A; Y(\gamma, \bar{\theta}))$, where
$\mathcal{L}$ denotes the negative log-likelihood function
of $F_{aggregate}(A)$.

Without use of $A_{aggregate}*(\gamma, \bar{\theta})$ as a prior, the native resolution pathlength estimate would be $A*(\gamma, \theta) = \operatorname{argmin}_A \mathcal{L}(A; Y(\gamma, \theta))$ (where $\theta$ is the view angle for either a low- or a high-energy exposure). The estimate of $A_{aggregate}*(\gamma, \bar{\theta})$ will be less noisy than $A*(\gamma, \theta)$ since more energy information is used. On the other hand, $A_{aggregate}*(\gamma, \bar{\theta})$ will represent a mix of two views and thus might result in a worsened spatial resolution and possibly aliasing artifacts if used directly in reconstruction when compared to using $A*(\gamma, \theta)$ for reconstruction. A tradeoff between spatial resolution and contrast can be achieved by adding a penalty function $\psi$, in the reconstruction:

$A*(\gamma,\theta) = \operatorname{argmin}_A \{ \mathcal{L}(A; Y(\gamma,\theta)) + \psi$
$(A - A_{aggregate}*(\gamma,\bar{\theta})) \}.$ For example, a penalty function could include $\psi(x) = \lambda \cdot x^2$ penalizing large deviations increasingly. The penalty function can be made dependent on imaging case (i.e. whether high spatial resolution or low noise in basis images is most desirable). For example, $\psi(x) = 0$ would result in native resolution, not utilizing the mixed view data for noise reduction.

The following non-limiting examples illustrate how three different procedures utilize the additional energy information available by combining dual energy with a switched kVp technique.

Example of a scheme for procedure 1:

1. Expose the object in a predetermined sequence of x-ray exposures where the acceleration voltage of the x-ray tube is changed several times during a rotation. One sequence (over views) could be low, low, high, low, low, high, . . . and another such sequence could be low, high, low, high, . . . etc.

2. Count photons interacting in the detection and increment bin counters based on which thresholds the deposited energy falls between.

3. The output is at least two subsets of projection data (counts in bins for each detector element and each view angle) acquired using different x-ray spectra.

4. Material basis decomposition is applied to the projection data resulting in pathlength estimates of basis materials (denoted $A^*(\gamma, \theta)$ for each detector element ($\gamma$) and view angle ($\theta$).

5. Different view angles $\theta$ will have seen a different pre-patient x-ray spectrum due to the switching of the acceleration voltage. Therefore, the covariance matrices of the pathlength estimates $A^*(\gamma, \theta)$ will be different.

6. The difference in covariance matrices (depending on actual x-ray spectrum used for the particular view angle $\theta$ can, but does not necessarily have to, be taken into consideration in reconstruction, possibly with an inverse weighting scheme based on the imaging task.

7. Basis images are reconstructed using the set of all or a subset thereof, possibly weighted, $A^*(\gamma, \theta)$, e.g. by some implementation of the inverse Radon transform.

Example of a scheme for procedure 2:

1. Expose the object in a predetermined sequence of x-ray exposures where the acceleration voltage of the x-ray tube is changed several times during a rotation. One sequence (over views) could be low, low, high, low, low, high, . . . and another such sequence could be low, high, low, high, . . . etc.

2. Count photons interacting in the detection and increment bin counters based on which thresholds the deposited energy falls between.

3. The output is at least two subsets of projection data (counts in bins for each detector element and each view angle) acquired using different x-ray spectra.

4. Counts in low-energy bins (in FIG. 5A and FIG. 5B between thresholds T1 and T2) are known to emanate from Compton interactions. Material basis decomposition, albeit with a penalty in spatial resolution since the view angles differ slightly between high- and low energy exposures, can be performed using the same method by which material decomposition is performed by switched kVp system utilizing energy-integrating detector today. This will result in pathlength estimates $A^*(\gamma, \tilde{\theta})$ where $\tilde{\theta}$ is an average view angle (average of the high and low energy x-ray exposures). These estimates will have a certain covariance matrix.

5. Material basis decomposition using the bin counts where photo-electric effect dominates (above T2 in FIG. 5) are performed based on the projection data resulting in pathlength estimates of basis materials (denoted $\theta$ for each detector element ($\gamma$) and view angle ($\theta$). This results in a set of $A^*(\gamma, \theta)$.

6. Different view angles $\theta$ will have seen a different pre-patient x-ray spectrum due to the switching of the acceleration voltage. Therefore, the covariance matrix of the pathlength estimates $A^*(\gamma, \theta)$ will be different, depending on which spectrum was applied in that view angle.

7. The difference in covariance matrices can, but does not necessarily have to, be taken into consideration in reconstruction, possibly with an inverse weighting scheme based on the imaging task.

8. Basis images are reconstructed using the set of all or a subset thereof, possibly weighted, $A^*(\gamma, \theta)$ and $A^*(\gamma, \theta)$, e.g. by some implementation of the inverse Radon transform.

Example of a scheme for procedure 3:

1. Expose the object in a predetermined sequence of x-ray exposures where the acceleration voltage of the x-ray tube is changed several times during a rotation. One sequence (over views) could be low, low, high, low, low, high, . . . and another such sequence could be low, high, low, high, . . . etc.

2. Count photons interacting in the detection and increment bin counters based on which thresholds the deposited energy falls between.

3. The output is at least two subsets of projection data (counts in bins for each detector element and each view angle) acquired using different x-ray spectra.

4. Group views based on the predetermined sequence of x-ray exposures. If "low, high, low, high, . . . etc" is the predetermined sequence and N energy bins are collected for each exposure, 2N bins for each average view angle $\tilde{\theta}$ are generated (but for fewer view angles).

5. Material basis decomposition is applied to the aggregated projection data (2N bins) resulting in pathlength estimates $A_{aggregate}^*(\gamma, \tilde{\theta})$ of basis materials. Due to the larger than native spacing of the average view angles $\tilde{\theta}$, this comes with a penalty in spatial resolution.

6. $A_{aggregate}^*(\gamma, \tilde{\theta})$ is used as prior information in a native resolution material basis decomposition, penalizing deviation of $A^*(\gamma, \theta)$ from $A_{aggregate}^*(\gamma, \tilde{\theta})$. In other words, when $A^*(\gamma, \theta)$, where $\theta$ is a view angle corresponding to either a high- or low-energy spectrum having been applied, is determined, information about $A_{aggregate}^*(\gamma, \theta)$, where $\tilde{\theta}$ is an average view angle of the high and low energy x-ray exposures, may be used, e.g. as previously described.

7. Basis images are reconstructed using the set of all or a subset thereof, possibly weighted, $A^*(\gamma, \theta)$, e.g. by some implementation of the inverse Radon transform.

For the interested reader, basis material decomposition generally utilizes the fact that all substances built up from elements with low atomic number, such as human tissue, have linear attenuation coefficients $\mu(E)$ whose energy dependence can be expressed, to a good approximation, as a linear combination of two basis functions:

$$\mu(E) = \alpha_1 f_1(E) + \alpha_2 f_2(E),$$

where $f_i$ are the basis functions and $\alpha_i$ are the corresponding basis coefficients. If there is one or more element in the imaged volume with high atomic number, high enough for a k-absorption edge to be present in the energy range used for the imaging, one basis function must be added for each such element. In the field of medical imaging, such k-edge elements can typically be iodine or gadolinium, substances that are used as contrast agents.

Basis material decomposition as such has been described in [8]. In basis material decomposition, the integral of each of the basis coefficients, $A_i = \int_l \alpha_i dl$ for $i=1, \ldots, N$ where N is the number of basis functions, is inferred from the measured data in each projection ray l from the source to a detector element. In one implementation, this is accomplished by first expressing the expected registered number of counts in each energy bin as a function of $A_i$:

$$\lambda_i = \int_{E=0}^{\infty} S_i(E) \exp\left(-\sum_{j=1}^{N} A_j f_j(E)\right) dE$$

Here, $\lambda_i$ is the expected number of counts in energy bin i, E is the energy, $S_i$ is a response function which depends on the spectrum shape incident on the imaged object, the quantum efficiency of the detector and the sensitivity of energy bin i to x-rays with energy E. Even though the term "energy bin" is most commonly used for photon-counting detectors, this formula can also describe other energy resolving x-ray systems such as multi-layer detectors or kVp switching sources.

Then, the maximum likelihood method may be used to estimate $A_i$, under the assumption that the number of counts in each bin is a Poisson distributed random variable. This is accomplished by minimizing the negative log-likelihood function, see Roessl and Proksa, K-edge imaging in x-ray computed tomography using multi-bin photon counting detectors, Phys. Med. Biol. 52 (2007), 4679-4696:

$$\hat{A}_1, \ldots, \hat{A}_N = \underset{A_1, \ldots, A_N}{\mathrm{argmin}} \sum_{i=1}^{M_b} \lambda_i(A_1, \ldots, A_N) - m_i \ln \lambda_i(A_1, \ldots, A_N)$$

where $m_i$ is the number of measured counts in energy bin i and $M_b$ is the number of energy bins.

When the resulting estimated basis coefficient line integral $\hat{A}_i$ for each projection line is arranged into an image matrix, the result is a material specific projection image, also called a basis image, for each basis i. This basis image can either be viewed directly (e.g. in projection x-ray imaging) or taken as input to a reconstruction algorithm to form maps of basis coefficients $\alpha_i$ inside the object (e.g. in CT). Anyway, the result of a basis decomposition can be regarded as one or more basis image representations, such as the basis coefficient line integrals or the basis coefficients themselves.

Figure 8B:
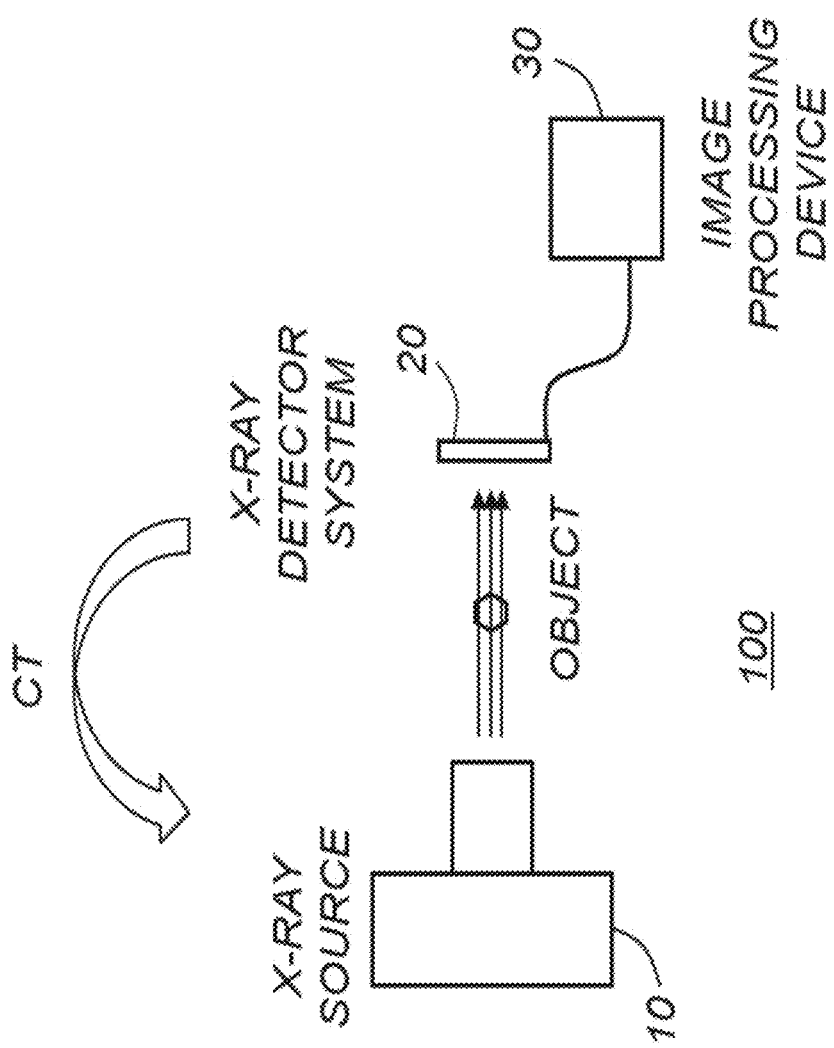
FIG. 8B is a schematic diagram illustrating an example of an overall x-ray imaging system according to an embodiment.

For completeness, it may be useful to provide a brief overview of an illustrative example of an overall x-ray imaging system, with reference to FIG. 8B, which is a schematic diagram illustrating an example of an overall x-ray imaging system according to an embodiment.

In this non-limiting example, the x-ray imaging system 100 basically comprises an x-ray source 10, an x-ray detector system 20 and an associated image processing device 30.

The x-ray source 10 emits x-rays, which pass through a subject or object to be imaged and are then registered by the x-ray detector system. Since some materials absorb a larger fraction of the x-rays than others, an image may be formed of the subject or object. The system is configured to enable kV-switched operation of the x-ray source 10.

In general, the x-ray detector system 20 is configured for registering radiation from the x-ray source 10 that may have been focused by optional x-ray optics and passed an object or subject or part thereof. The x-ray detector system 20 is connectable to the image processing device 30 via suitable analog processing and read-out electronics (which may be integrated in the x-ray detector system 20) to enable image processing, such as basis material decomposition and/or image reconstruction by the image processing device 30.

An example of a commonly used x-ray imaging system is a Computed Tomography (CT) system, which may include an x-ray source that produces a fan or cone beam of x-rays and an opposing x-ray detector system for registering the fraction of x-rays that are transmitted through a patient or object. The x-ray source and detector system are normally mounted in a gantry that rotates around the imaged object.

Accordingly, the x-ray source 10 and the x-ray detector system 20 illustrated in FIG. 8A and FIG. 8B may thus be arranged as part of a CT system, e.g. mountable in a CT gantry.

In this example, the x-ray detector system 20 is a photon-counting multi-bin detector, and the image processing device 30 may receive photon count information from the x-ray detector 20 as input for basis material decomposition and/or image reconstruction as described herein.

Figure 8C:
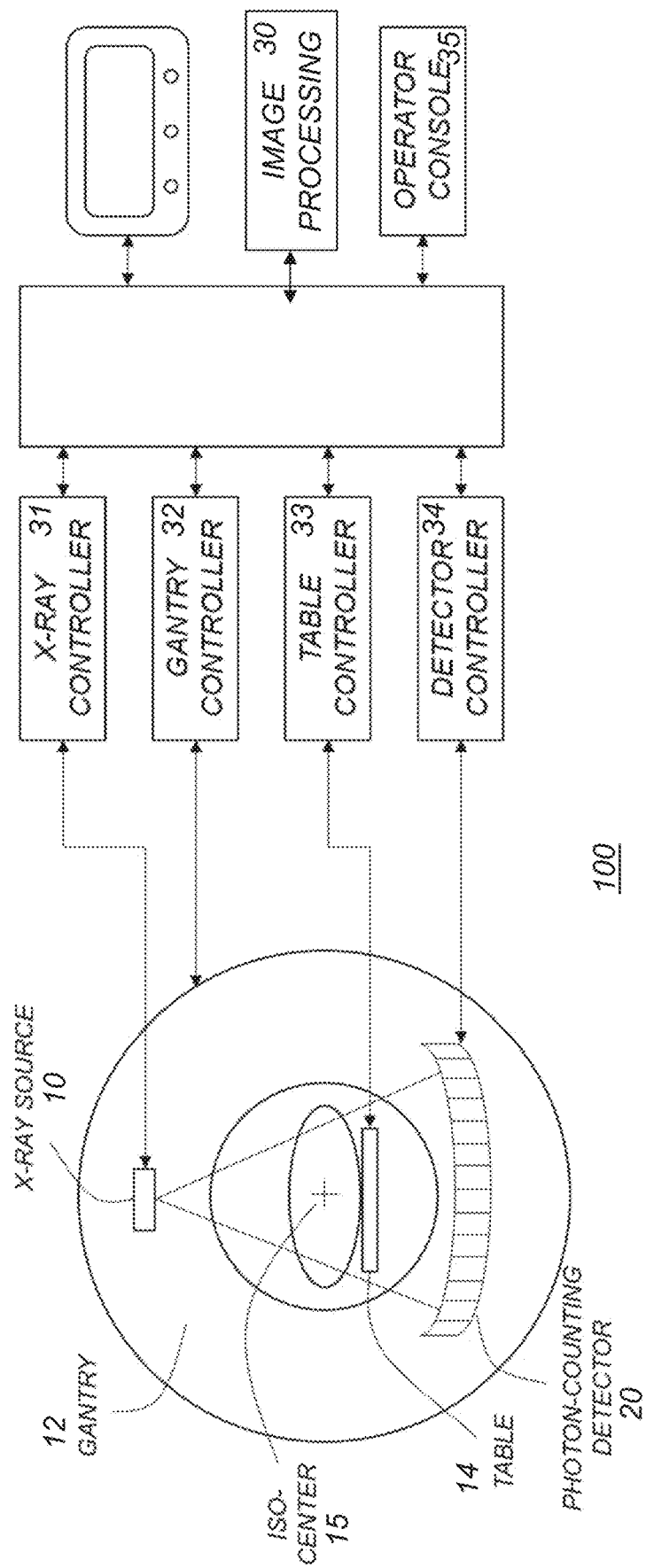
FIG. 8C is a schematic diagram illustrating another example of an overall x-ray imaging system according to an embodiment.

FIG. 8C is a schematic diagram illustrating another example of an overall x-ray imaging system according to an embodiment. In this example, the x-ray imaging system 100 comprises an x-ray source 10, a gantry 12, and a patient table 14, an x-ray detector system 20, an associated image processing device 30, various controllers 31, 32, 33, 34, an operator console 35 and a display.

In this example, the x-ray source 10 and x-ray detector system 20 are mounted in a gantry 12 that rotates with respect to an iso-center 15.

In this non-limiting example, the various controllers include an x-ray controller 31 for controlling the x-ray source, e.g. for switching it on and off, and for controlling the mode of operation such as kV-switched mode. The system 100 also includes a gantry controller 32 and a table controller 33, e.g. for controlling the movements and rotation of the gantry and the table, respectively. There is also a detector controller 34 for controlling the operations of the photon-counting multi-bin detector 20 including read-out of photon count information and other possible detector output.

In this embodiment, also, the x-ray detector system 20 is connectable to the image processing device 30 via suitable analog processing and read-out electronics and analog and/or digital data paths to enable image processing, basis material decomposition and/or image reconstruction by the image processing device 30.

The system 100 may also include an operator console 35 with an associated display for allowing an operator to interact with the system.

It will be appreciated that the methods and devices described herein can be combined and re-arranged in a variety of ways.

For example, specific functions may be implemented in hardware, or in software for execution by suitable processing circuitry, or a combination thereof.

The steps, functions, procedures, modules and/or blocks described herein may be implemented in hardware using any conventional technology, such as semiconductor technology, discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs).

Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

Figure 9:
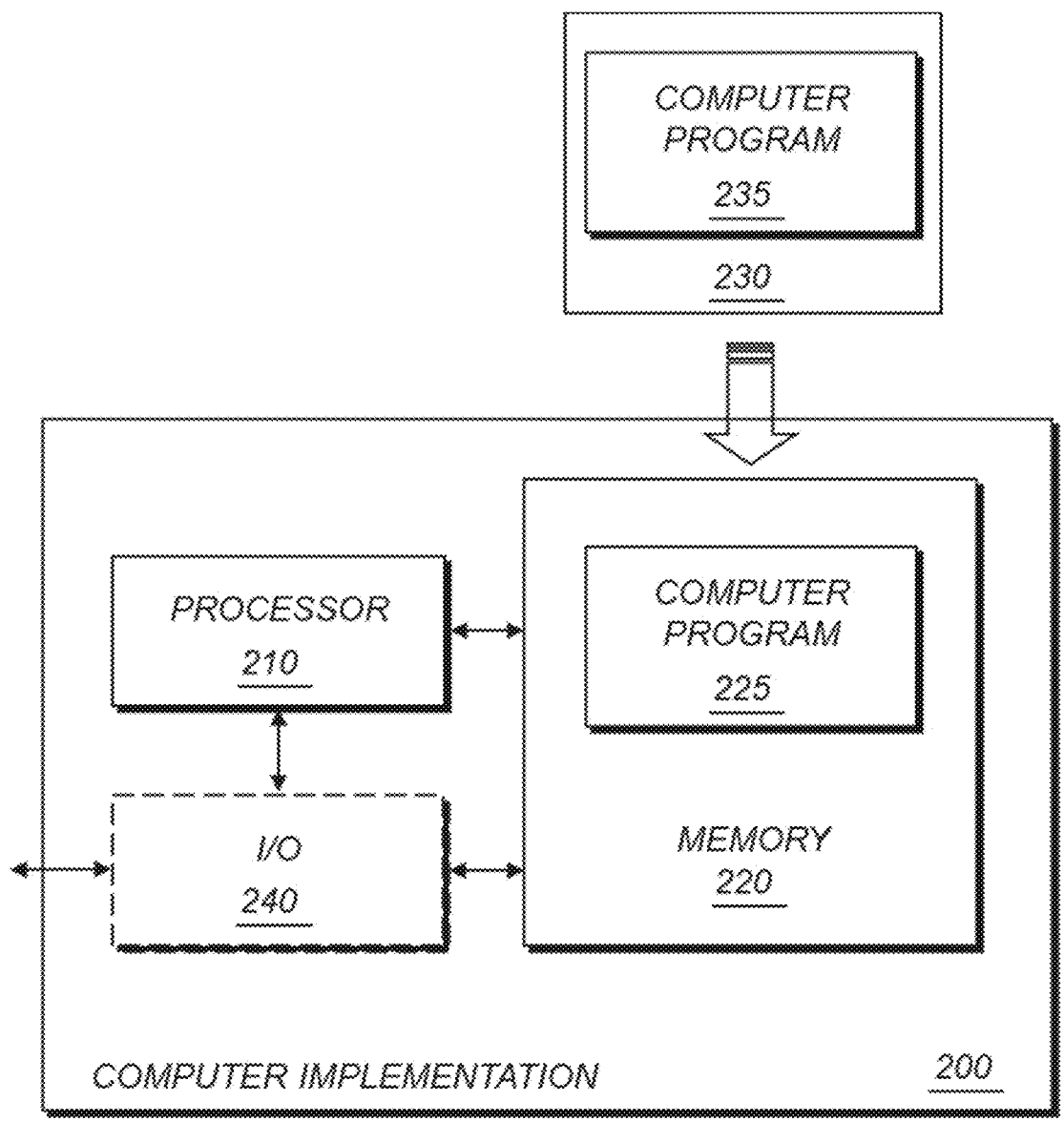
FIG. 9 is a schematic diagram illustrating an example of a computer implementation according to an embodiment.

FIG. 9 is a schematic diagram illustrating an example of a computer implementation according to an embodiment.

In this particular example, the system 200 comprises a processor 210 and a memory 220, the memory comprising instructions executable by the processor, whereby the processor is operative to perform computer-implementable steps and/or actions described herein. The instructions are typically organized as a computer program 225; 235, which may be preconfigured in the memory 220 or downloaded from an external memory device 230. Optionally, the system 200 comprises an input/output interface 240 that may be interconnected to the processor(s) 210 and/or the memory 220 to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks. The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

Method flows or relevant parts thereof may be regarded as computer action flows, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively, it is possibly to realize the modules predominantly by hardware modules, or alternatively by hardware. The extent of software versus hardware is purely implementation selection.

The embodiments described above are merely given as examples, and it should be understood that the proposed technology is not limited thereto. It will be understood by those skilled in the art that various modifications, combinations and changes may be made to the embodiments without departing from the invention. In particular, different part solutions in the different embodiments can be combined in other configurations, where technically possible.

REFERENCES

1. US2012/0087463
2. U.S. Pat. No. 9,757,085
3. U.S. Pat. No. 9,836,859
4. Sebastian Faby, Stefan Kuchenbecker, Stefan Sawall, David Simons, Heinz-Peter Schlemmer, Michael Lell, Marc Kachelrieß, "Performance of today's dual energy CT and future multi energy CT in virtual non-contrast imaging and in iodine quantification: A simulation study", Medical Physics 42 (7), July 2015, doi: http://dx.doi.org/10.1118/1.4922654.
5. Tao, A, Huang, R, Tao, S, Michalak, G, McCollough, C, Leng, S. Dual Source Photon-Counting-Detector CT with a Tin Filter: A Phantom Study on Iodine Quantification Accuracy and Precision. Radiological Society of North America 2018 Scientific Assembly and Annual Meeting. Nov. 25-Nov. 30, 2018, Chicago Ill. archive.rsna.org/2018/18014541.html Accessed Feb. 18, 2019.
6. Robert E. Alvarez "Estimator for photon counting energy selective x-ray imaging with multibin pulse height analysis", Med. Phys. 38 (5), May 2011.
7. Ehn, S, Sellerer, T, Mechlem, K, Fehringer, A, Epple, M, Herzen, J, Pfeiffer, F, Noël, P B, "Basis material decomposition in spectral CT using a semi-empirical, polychromatic adaption of the Beer-Lambert model", Phys. Med. Biol. 62, 2017.
8. Alvarez and Macovski, "Energy-selective reconstructions in X-ray computerised tomography", Phys. Med. Biol. 21, 733.

The invention claimed is:

1. An apparatus for x-ray imaging comprising:
an x-ray source and an x-ray detector having a plurality of detector elements, the x-ray source and the x-ray detector being disposed on a support that is configured to rotate around a subject or object to be imaged to enable a set of projections at different view angles,
wherein the x-ray source is configured to be operated in switched kVp mode to alternately apply at least two different voltages including a lower voltage and a higher voltage during rotation to enable lower-energy and higher-energy exposures over the set of projections, thereby providing for lower-energy projections and higher-energy projections,
wherein the x-ray detector is a photon-counting multi-bin detector configured to allocate photon counts to a plurality of energy bins, and the apparatus is configured to select counts from at least a subset of the plurality of energy bins to provide corresponding photon count information for both lower-energy projections and higher-energy projections,
wherein the apparatus is configured to perform material basis decomposition for each of one or more of (i) a plurality of the lower-energy projections and higher-energy projections, and (ii) a plurality of combinations of at least one lower-energy projection and at least one higher-energy projection, based on the corresponding photon count information, wherein the apparatus is configured to perform said material basis decomposition to generate pathlength estimates of basis materials for each of one or more of (i) the plurality of lower-energy projections and the plurality of higher-energy projections, and (ii) the plurality of combinations of the at least one lower-energy projection and the at least one higher-energy projection, and to perform image reconstruction based on the pathlength estimates, and wherein the apparatus is configured to generate the pathlength estimates of basis materials and associated covariance matrices representing covariance of the pathlength estimates, and to combine the pathlength estimates for lower-energy and higher-energy projections based on the corresponding covariance matrices.

2. The apparatus of claim 1, wherein the apparatus is configured to provide kV-switching to alternately apply at least two different voltages to the x-ray source during a rotation.

3. The apparatus of claim 1, wherein the photon-counting multi-bin detector is configured to allocate, for each of the projections including for each of the detector elements and each of the view angles, under a lower-energy exposure or a higher-energy exposure, photon counts to energy bins, and the apparatus is configured to extract counts from at least a subset of the energy bins to provide corresponding photon count information for the projection.

4. The apparatus of claim 1, wherein the apparatus is configured to perform material basis decomposition based on information about an applied x-ray spectrum.

5. The apparatus of claim 1, wherein the apparatus is configured to generate a dual energy path length estimate based on adjacent projections, including photon count information of at least one of the lower-energy projections and at least one of the higher-energy projections.

6. The apparatus of claim 5, wherein the apparatus is configured to use said dual energy path length estimate as prior information to optimize a trade-off between spatial resolution and basis image noise.

7. The apparatus of claim 1, wherein the apparatus is configured to selectively perform a weighting procedure in dependence on a selected imaging task.

8. The apparatus of claim 1, wherein thresholds of the photon counting multi-bin detector are allocated such that one or more bins are allocated to count the Compton part of the spectrum and the remainder is allocated to the photo-electric part of the spectrum.

9. The apparatus of claim 1, wherein thresholds of the photon counting multi-bin detector for the higher-energy projections and the lower-energy projections are the same.

10. The apparatus of claim 1, wherein thresholds of the photon counting multi-bin detector for the lower-energy projections differ from thresholds for the higher-energy projections.

11. The apparatus of claim 1, wherein the photon-counting multi-bin detector is based on a direct conversion material.

12. The apparatus of claim 11, wherein the photon-counting multi-bin detector is provided with silicon as the direct conversion material.

13. An x-ray imaging system comprising:
an apparatus for x-ray imaging comprising:
an x-ray source and an x-ray detector having a plurality of detector elements, the x-ray source and the x-ray detector being disposed on a support that is configured to rotate around a subject or object to be imaged to enable a set of projections at different view angles, wherein the x-ray source is configured to be operated in switched kVp mode to alternately apply at least two different voltages including a lower voltage and a higher voltage during rotation to enable lower-energy and higher-energy exposures over the set of projections, thereby providing for lower-energy projections and higher-energy projections, wherein the x-ray detector is a photon-counting multi-bin detector configured to allocate photon counts to a plurality of energy bins, and the apparatus is configured to select counts from at least a subset of the plurality of energy bins to provide corresponding photon count information for both lower-energy projections and higher-energy projections, wherein the apparatus is configured to perform material basis decomposition for each of one or more of (i) a plurality of the lower-energy projections and higher-energy projections and (ii) a plurality of combinations of at least one lower-energy projection and at least one higher-energy projection, based on the corresponding photon count information, wherein the apparatus is configured to perform said material basis decomposition to generate pathlength estimates of basis materials for each of one or more of (i) the plurality of lower-energy projections and the plurality of higher-energy projections and (ii) the plurality of combinations of the at least one lower-energy projection and the at least one higher-energy projection, and to perform image reconstruction based on the pathlength estimates, and wherein the apparatus is configured to generate the pathlength estimates of basis materials and associated covariance matrices representing covariance of the pathlength estimates, and to combine the pathlength estimates for lower-energy and higher-energy projections based on the corresponding covariance matrices.

14. The x-ray imaging system of claim 13, wherein one or more of (i) the x-ray imaging system and (ii) the apparatus for x-ray imaging is a Computed Tomography (CT) system.

15. The apparatus of claim 2, wherein the photon-counting multi-bin detector is configured to allocate, for each of the projections including for each of the detector elements and each of the view angles, under a lower-energy exposure or a higher-energy exposure, photon counts to energy bins, and the apparatus is configured to extract counts from at least a subset of the energy bins to provide corresponding photon count information for the projection.

16. The apparatus of claim 2, wherein the apparatus is configured to perform material basis decomposition based on information about an applied x-ray spectrum.

17. The apparatus of claim 3, wherein the apparatus is configured to perform material basis decomposition based on information about an applied x-ray spectrum.

* * * * *